US011723910B1

(12) United States Patent
Breslin et al.

(10) Patent No.: US 11,723,910 B1
(45) Date of Patent: Aug. 15, 2023

(54) COMPOSITIONS AND METHODS FOR MODULATING THE ENDOTHELIAL BARRIER (71) Applicant: University of South Florida, Tampa, FL (US)

(72) Inventors: Jerome William Breslin, Tampa, FL (US); Zeinab Yehia Khalil Motawe, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 16/986,188

(22) Filed: Aug. 5, 2020

Related U.S. Application Data (60) Provisional application No. 62/882,721, filed on Aug. 5, 2019.

(51) Int. Cl.
*A61K 31/5375* (2006.01)
*A61K 31/499* (2006.01)
*A61K 31/155* (2006.01)
*A61K 31/341* (2006.01)
*A61K 31/4015* (2006.01)
*A61K 31/445* (2006.01)
*A61K 31/15* (2006.01)
*A61K 31/485* (2006.01)
*A61K 31/4045* (2006.01)
*A61K 31/343* (2006.01)

(52) U.S. Cl.
CPC .......... *A61K 31/5375* (2013.01); *A61K 31/15* (2013.01); *A61K 31/155* (2013.01); *A61K 31/341* (2013.01); *A61K 31/343* (2013.01); *A61K 31/4015* (2013.01); *A61K 31/4045* (2013.01); *A61K 31/445* (2013.01); *A61K 31/485* (2013.01); *A61K 31/499* (2013.01)

(58) Field of Classification Search
CPC .......... A61K 31/5375; A61P 9/10; A61P 7/10; A61P 29/00
USPC .......................................... 514/238.8, 239.5
See application file for complete search history.

(56) References Cited

PUBLICATIONS

Allahtavakoli, M. et al.: Effect of delayed stimulation of sigma-1 receptor on embolic model of ischemia in rats. J. Babol Univ. Med. Sci., vol. 13, pp. 40-47, 2011.*
Hosszu, A. et al.: Sigma-1 receptor agonism protects against renal ischemia-reperfusion injury. Journal of the American Soc. of Nephrology, vol. 28, pp. 152-165, 2017.*
Shen, Y-C. et al.: Dimemorphan protects rats against ischemic stroke through activation of sigma-1 receptor-mediated mechanism by decreasing glutamate accumulation. Journal of Neurochemistry, vol. 104, pp. 558-572, 2008.*
Dong, H et al.: Sigma - 1 receptor modulates neuroinflammation after traumatic brain injury. Cell. Mol. Neurobiol., vol. 36, pp. 639-645, 2016.*
Vogler, S. et al.: Sigma-1 receptor activation inhibits osmotic swelling of rat retinal glial cells by transactivation of gltamatergic and purinergic receptors. Neurosci. Lett., vol. 610, pp. 13-18, 2016.*
Alves NG, Trujillo AN, Breslin JW, & Yuan SY (2018) Sphingosine-1-Phosphate Reduces Hemorrhagic Shock and Resuscitation-Induced Microvascular Leakage by Protecting Endothelial Mitochondrial Integrity. Shock.52:4, pp. 423-433.
Bhuiyan MS, Tagashira H, Shioda N, & Fukunaga K (2010) Targeting sigma-1 receptor with fluvoxamine ameliorates pressure-overload-induced hypertrophy and dysfunctions. Expert Opin Ther Targets 14(10):1009-1022.
Breslin JW, Zhang XE, Worthylake RA, & Souza-Smith FM (2015) Involvement of local lamellipodia in endothelial barrier function. PLoS One 10(2):e0117970.
Cao J, et al. (2017) Polarized actin and VE-cadherin dynamics regulate junctional remodelling and cell migration during sprouting angiogenesis. Nat Commun 8(1):2210.
Cruys B, et al. (2016) Glycolytic regulation of cell rearrangement in angiogenesis. Nat Commun 7:12240.
De Bock K, et al. (2013) Role of PFKFB3-driven glycolysis in vessel sprouting. Cell 154(3):651-663.
Eelen G, de Zeeuw P, Simons M, & Carmeliet P (2015) Endothelial cell metabolism in normal and diseased vasculature. Circ Res 116(7):1231-1244.
Hayashi T & Su TP (2007) Sigma-1 receptor chaperones at the ER-mitochondrion interface regulate Ca(2+) signaling and cell survival. Cell 131(3):596-610.
Liu DY, et al. (2018) Sigma-1 receptor activation alleviates blood-brain barrier dysfunction in vascular dementia mice. Exp Neurol 308:90-99.
Mavlyutov TA, et al. (2017) The Sigma-1 Receptor—A Therapeutic Target for the Treatment of ALS? Adv Exp Med Biol 964:255-265.
Nieminen AL, Saylor AK, Herman B, & Lemasters JJ (1994) ATP depletion rather than mitochondrial depolarization mediates hepatocyte killing after metabolic inhibition. Am J Physiol 267(1 Pt 1):C67-74.
Rellick SL, Hu H, Simpkins JW, & Ren X (2016) Evaluation of Bioenergetic Function in Cerebral Vascular Endothelial Cells. J Vis Exp (117).
Smith SB, et al. (2018) Sigma 1 receptor: A novel therapeutic target in retinal disease. Prog Retin Eye Res 67:130-149.
Trujillo AN, et al. (2017) Modulation of mesenteric collecting lymphatic contractions by sigma1-receptor activation and nitric oxide production. Am J Physiol Heart Circ Physiol 313(4):H839-H853.
Unno N, et al. (1996) Hyperpermeability and ATP depletion induced by chronic hypoxia or glycolytic inhibition in Caco-2BBe monolayers. Am J Physiol 270(6 Pt 1):G1010-1021.

(Continued)

*Primary Examiner* — Charanjit Aulakh
(74) *Attorney, Agent, or Firm* — Meunier Carlin & Curfman LLC (57) ABSTRACT

Disclosed are compositions and methods for modulating endothelial barrier function.

3 Claims, 5 Drawing Sheets

Specification includes a Sequence Listing.

(56) References Cited

PUBLICATIONS

Zamanillo D, Romero L, Merlos M, & Vela JM (2013) Sigma 1 receptor: a new therapeutic target for pain. Eur J Pharmacol 716(1-3):78-93.

Zecchin A, Kalucka J, Dubois C, & Carmeliet P (2017) How Endothelial Cells Adapt Their Metabolism to Form Vessels in Tumors. Front Immunol 8:1750.

Zhang XF, Adderley SP, & Breslin JW (2016) Activation of RhoA, but Not Rac1, Mediates Early Stages of S1P-Induced Endothelial Barrier Enhancement. PLoS One 11(5):e0155490.

* cited by examiner

COMPOSITIONS AND METHODS FOR MODULATING THE ENDOTHELIAL BARRIER

CROSS REFERENCE TO RELATED APPLICATIONS

This application claims the benefit of priority to U.S. Provisional Patent Application No. 62/882,721, filed Aug. 5, 2019, the entire contents of which are fully incorporated herein by reference.

STATEMENT REGARDING GOVERNMENT SUPPORT

This invention was made with government support under grant no. R01GM120774 awarded by National Institutes of Health/National Institute of General Medical Sciences. The government has certain rights in the invention.

FIELD

The present disclosure relates to compositions and methods for modulating endothelial barrier.

BACKGROUND

Many diseases involve the production of reactive oxygen species, which can arise due to inflammation and/or ischemia. In the endothelium, this can lead to dysfunction of the enzyme endothelial nitric oxide synthase (eNOS) to promote additional reactive oxygen species production and can also lead to impairment of the normal barrier function that prevents the formation of edema.

Bioenergetic function within endothelial cells are thought to contribute to vascular barrier integrity (Rellick S L, et al., (2016) Evaluation of Bioenergetic Function in Cerebral Vascular Endothelial Cells. *J Vis Exp* (117)). It was recently found that inhibition of mitochondrial complex 3 disrupts endothelial barrier function (Alves N G, et al. (2018) Sphingosine-1-Phosphate Reduces Hemorrhagic Shock and Resuscitation-Induced Microvascular Leakage by Protecting Endothelial Mitochondrial Integrity. *Shock*). However, endothelial cells can rely more on glycolysis for energy production than mitochondrial oxidative phosphorylation as a measure to spare oxygen for delivery to the surrounding tissues (Eelen G, et al., (2015) Endothelial cell metabolism in normal and diseased vasculature. *Circ Res* 116(7): 1231-1244). Therefore, what is needed is a composition and a method of modulating vascular barrier function and treating diseases involving impaired endothelial cell barrier function. The compositions and methods disclosed herein address these and other needs.

SUMMARY

In accordance with the purposes of the disclosed materials and methods, as embodied and broadly described herein, the disclosed subject matter, in one aspect, relates to compounds, compositions and methods of making and using compounds and compositions.

In some aspects, disclosed herein is a method of modulating (e.g., enhancing) endothelial barrier function in a subject in need thereof, comprising: administering to the subject a therapeutically effective amount of a sigma-1 receptor agonist or a pharmaceutically acceptable salt thereof.

In some embodiments, the sigma-1 receptor is expressed in an endothelial cell. In some embodiments, the endothelial cell comprises an arterial endothelial cell, a pulmonary endothelial cell, a venous endothelial cell, a capillary endothelial cell, or a lymphatic endothelial cell.

In some embodiments, the sigma-1 receptor agonist is selected from the group consisting of PRE-084, SA-4503, ditolylguanidine, afobazole, fluvoxamine, donepezil, anavex 2-73, citalopram, amitriptyline, L-687,384, dextromethorphan, dimethyltryptamine, and (+)- pentazocine, and the allosteric modulator methylphenylpiracetam.

In some embodiments, the subject in a human. In some embodiments, the human has an endothelial barrier disorder relating to dysregulated ATP metabolism. In some embodiments, the endothelial barrier disorder comprises ischemia, sepsis, edema, or inflammatory bowel disease.

In some further aspects, disclosed herein is a method of treating ischemia in a subject in need thereof, comprising: administering to the subject a therapeutically effective amount of a sigma-1 receptor agonist or a pharmaceutically acceptable salt thereof.

The details of one or more embodiments of the invention are set forth in the accompanying drawings and the description below. Other features, objects, and advantages of the invention will be apparent from the description and drawings, and from the claims.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF DRAWINGS

The accompanying figures, which are incorporated in and constitute a part of this specification, illustrate several aspects described below.

FIGS. 1A-1I show σ1 and endothelial barrier function. FIG. 1A depicts traces showing the time course of TER changes in HUVEC treated with the shown concentrations of PRE-084. FIG. 1B shows the bar graph represents the differences in TER after 1 h of PRE-084. N=4/group. FIG. 1C shows traces of TER over time in cell treated with 10 μM CCCP, with or without 5 min 100 μM PRE-084 pretreatment. FIG. 1D shows mean TER differences at 4 h between groups. FIG. 1E shows traces of TER changes in cells with siRNA knockdown of σ1 (σ1 kd) vs. non-targeting RNA transfection (NT). Insets show western blot images of σ1 expression at 48 h and 70 h respectively. FIG. 1F shows comparison of mean TER at 70 h for the σ1 kd and NT groups. FIG. 1G shows mean and intensities of σ1 normalized to (β-actin for the σ1 kd and NT groups at 48 h and 70 h (n=4/group). FIG. 1H shows traces of TER over time for σ1 kd and NT cells treated with 10 μM CCCP or vehicle. FIG. 1I shows comparison of TER at 3 h for the groups shown in FIG. 1H. *p<0.05; ANOVA, Dunnett's and t-tests used for analysis.

FIGS. 2A-2K show that PRE-084 enhances glycolytic ATP production in HUVEC.

FIGS. 3A and 3B show that PRE-084 elevates barrier function of human dermal microvascular endothelial cell (HDMEC) monolayers.

FIGS. 4A-4D shows that PRE-084 partially rescues TER drop in IL-1β treated cells. FIG. 4A shows traces of changes in TER with time in IL-1β 15 ng/ml treated cells in presence or absence of PRE-084 100 µM. PRE-084 was added at time=0 followed by IL-1β 5 min after. FIG. 4B shows scatter blot representing TER differences at 3 h. Sigma-1 receptor kd cells have less TER in response to inflammatory challenge. FIG. 4C shows traces of the changes in TER of HUVEC cells transfected with sigmar1 siRNA or non-targeting RNA (control) in response to IL-1β 15 ng/ml or vehicle added at time 0. FIG. 4D shows scatter blot representing difference in TER at 2 h between non-targeting transfected cells and sigmar1 kd cells exposed to IL-1β.

FIGS. 5A and 5B show that PRE-84 elevates barrier function of human lung microvascular endothelial cell (HLMEC) monolayers.

FIGS. 6A and 6B show that DTG elevates barrier function of human umbilical vein endothelial cell (HUVEC) monolayers.

FIGS. 7A-7F show that Afobazole enhances glycolytic proton efflux rate (FIG. 7A) and lowers oxygen consumption rate in HUVEC (FIG. 7B).

DETAILED DESCRIPTION

The materials, compounds, compositions, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

Terms used throughout this application are to be construed with ordinary and typical meaning to those of ordinary skill in the art. However, Applicant desires that the following terms be given the particular definition as defined below.

Terminology

As used in the specification and claims, the singular form "a," "an," and "the" include plural references unless the context clearly dictates otherwise. For example, the term "an agonist" includes a plurality of agonist, including mixtures thereof.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

"Administration" to a subject includes any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation or via an implanted reservoir, and the like. Administration includes self-administration and the administration by another.

As used herein, the term "comprising" is intended to mean that the compositions and methods include the recited elements, but not excluding others. "Consisting essentially of" when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions of this invention. Embodiments defined by each of these transition terms are within the scope of this invention.

As used herein, the term "endothelial barrier" refers to the layer of cells lining various organs and cavities of the body, including, for example, blood vessels, heart, and lymphatic vessels, and act as a selective barrier between the vessel lumen and surrounding tissue, by controlling the transit of fluids, materials and cells such as myeloid cells and white blood cells across the barrier.

The term "modulating endothelial barrier function" means any treatment aiming at maintaining the endothelium in a quiescent inactivated anti-coagulant state and maintaining the endothelial cell barrier by avoiding or limiting permeability of said barrier.

The term "ischemia" refers to any conditions that result from a restriction in blood supply in at least one organ or tissue. These conditions typically result from the obstruction of a blood vessel. For example, ischemia includes but is not limited to renal ischemia, retinal ischemia, brain ischemia and myocardial ischemia. More particularly, the term includes but it is not limited global cerebral ischemia due to cardiac arrest, focal cerebral infarction, cerebral hemorrhage, hemorrhage infarction, hypertensive hemorrhage, hemorrhage due to rupture of intracranial vascular abnormalities, subarachnoid hemorrhage due to rupture of intracranial arterial aneurysms, hypertensive encephalopathy, carotid stenosis or occlusion leading to cerebral ischemia, cardiogenic thromboembolism, spinal stroke and spinal cord injury, diseases of cerebral blood vessels: e.g., atherosclerosis, vasculitis, macular degeneration, myocardial infarction, cardiac ischemia and superaventicular tachyarrhytmia.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be an about 1, 5, 10, 20, 30, 40, 50, 60, 70, 80, 90, 100%, or any amount of reduction in between as compared to native or control levels.

The terms "prevent," "preventing," "prevention," and grammatical variations thereof as used herein, refer to a method of partially or completely delaying or precluding the onset or recurrence of a disease and/or one or more of its attendant symptoms or barring a subject from acquiring or reacquiring a disease or reducing a subject's risk of acquiring or reacquiring a disease or one or more of its attendant symptoms.

The term "agonist" refers to a composition that binds to a receptor and activates the receptor to produce a biological response. The terms also encompass pharmaceutically acceptable, pharmacologically active derivatives of agonists specifically mentioned herein, including, but not limited to, salts, esters, amides, proagents, active metabolites, isomers, fragments, analogs, and the like. When the term "agonist" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc. Accordingly, the term "sigma-1 receptor agonist" can include any one or more agents which upon administration to a subject, can activate sigma-1 receptor.

The term "subject" refers to a human in need of treatment for any purpose, and more preferably a human in need of treatment to treat a disease or disorder, such as ischemia. The term "subject" can also refer to non-human animals, such as dogs, cats, horses, cows, pigs, sheep and non-human primates, among others.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia, Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

"Therapeutically effective amount" or "therapeutically effective dose" of a composition (e.g. PRE-084) refers to an amount that is effective to achieve a desired therapeutic result. In some embodiment, a desired therapeutic result is the increase of endothelial barrier integrity. In some embodiment, a desired therapeutic result is the treatment of ischemia, sepsis, edema, or inflammatory bowel disease. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Reference will now be made in detail to specific aspects of the disclosed materials, compounds, compositions, articles, and methods, examples of which are illustrated in the accompanying Examples and Figures.

Compounds and Methods

Disclosed is the sigma-1-mediated modulation of endothelial barrier function, focusing on a bioenergetics mechanism due to its subcellular location at the mitochondria-associated endoplasmic reticulum membrane. Sigma-1 protects endothelial cells from barrier disruption caused by the mitochondrial H+ ionophore carbonyl cyanide m-chlorophenyl hydrazine (CCCP), which depletes cellular energy without blocking a specific mitochondrial complex (Nieminen A L, et al., (1994) ATP depletion rather than mitochondrial depolarization mediates hepatocyte killing after metabolic inhibition. *Am J Physiol* 267(1 Pt 1):C67-74), mimicking ischemia. Thus, sigma-1 can protect the endothelial barrier by stabilizing cellular energy production. The disclosed data show the use of agents that selectively activate sigma receptor-1, such as, but not limited to, PRE-084, SA-4503, ditolylguanidine, and afobazole, for treatment of endothelial barrier disorders by shifting metabolic production of ATP from oxidative mechanisms toward anaerobic glycolysis. These findings are applicable to endothelial barrier disorders relating to dysregulated ATP metabolism, including but not limited to diabetes, peripheral vascular disease, heart disease, hypertension, venous thrombosis, insulin resistance, ischemic diseases of gut, stroke, sepsis, edema, inflammatory bowel disease, chronic inflammatory diseases, and sever viral infectious disease.

In some aspects, disclosed herein are methods of modulating endothelial barrier function in a subject in need thereof, comprising: administering to the subject a therapeutically effective amount of a sigma-1 receptor agonist or a pharmaceutically acceptable salt thereof. In some embodiments, the sigma-1 receptor agonist is selected from the group consisting of PRE-084, SA-4503, ditolylguanidine, and afobazole. This sigma-1 receptor agonist can be useful for treating, preventing, reducing endothelial barrier disorders (such as, ischemia, sepsis, edema, or inflammatory bowel disease) relating to dysregulation of ATP metabolism. Accordingly, in some aspects, disclosed herein is a method of modulating endothelial barrier function in a subject in need thereof, comprising: administering to the subject a therapeutically effective amount of a sigma-1 receptor agonist or a pharmaceutically acceptable salt thereof.

"Endothelial barrier disorder" refers herein to a local or systemic pathological state of endothelial barrier and can be broadly defined as an imbalance between vasodilating and vasoconstricting substances as well as pro- and anti-coagulant substances produced by (or acting on) the endothelial cells. In addition, excessive or prolonged increases in permeability of vascular endothelial cell barrier leads to tissue edema/swelling. Therefore, "modulating endothelial barrier function" used herein refers to a treatment (for example, administering to a subject a therapeutically effective amount of a sigma-1 receptor agonist) aiming at maintaining the endothelium in a quiescent inactivated anti-coagulant state and maintaining and/or improving the endothelial cell barrier integrity by avoiding or limiting permeability of said barrier. In some embodiments, the term "modulating endothelial barrier function" means the maintenance of the vascular endothelial barrier integrity by avoiding, limiting, or reducing permeability of said barrier. In some embodiments, the term "enhancing endothelial barrier function" means the enhancement of the vascular endothelial barrier integrity by avoiding, limiting, or reducing permeability of said barrier. Methods of enhancing endothelial barrier function are also disclosed herein.

In some embodiments, the endothelial cell comprises an arterial endothelial cell, a pulmonary endothelial cell, a venous endothelial cell, a capillary endothelial cell, or a lymphatic endothelial cell. In some embodiments, the endothelial cell is an arterial endothelial cell. In some endothelial cell is a pulmonary endothelial cell. In some embodiments, the endothelial cell is a venous cell. In some embodiments, the endothelial cell is a capillary endothelial cell. In some embodiments, the endothelial cell is a lymphatic endothelial cell. In some embodiments, the sigma-1 receptor is expressed in an endothelial cell.

It should also be understood that "sigma-1 receptor" refers herein to a polypeptide that synthesizes and hydrolyzes cyclic adenosine 5'-diphosphate-ribose, and in humans is encoded by the SIGMAR1 gene. In some embodiments, the sigma-1 receptor polypeptide is that identified in one or more publicly available databases as follows: HGNC: 8157, Entrez Gene: 10280, Ensembl: ENSG00000147955, OMIM: 601978, UniProtKB: Q99720. In some embodiments, the sigma-1 receptor polypeptide comprises the sequence of SEQ ID NO:1, or a polypeptide sequence having at or greater than about 80%, about 85%, about 90%, about 95%, or about 98% homology with SEQ ID NO:1, or a polypeptide comprising a portion of SEQ ID NO:1. The sigma-1 receptor polypeptide of SEQ ID NO:1 may represent an immature or pre-processed form of mature sigma-1 receptor, and accordingly, included herein are mature or processed portions of the sigma-1 receptor polypeptide in SEQ ID NO:1. The sigma-1 receptor is a small (28 kDa), highly conserved, transmembrane protein located in the endoplasmic reticulum membrane. The sigma-1 receptor is shown to locate at or in neuronal nuclear, mitochondrial, and plasma membranes. The sigma-1 receptor is ubiquitously expressed. The sigma-1 receptor is widely expressed in, for example, the central nervous system, liver, kidneys, and lungs, in the endocrine, immune and reproductive tissues, indicating multiple pathways by which these receptors may influence physiological and pathological processes.

Accordingly, it is understood and herein contemplated that the term "sigma-1 receptor agonist" refers to any one or more agents which upon administration to a subject, can activate sigma-1 receptor. In some embodiments, the sigma-1 receptor agonist is selected from the group consisting of PRE-084, SA-4503, ditolylguanidine, and afobazole. It should be understood that "sigma-1 receptor agonist" encompasses pharmaceutically acceptable, pharmacologi- cally active derivatives of agonists specifically mentioned herein (e.g., PRE-084, SA-4503, ditolylguanidine, or afobazole), including, but not limited to, salts, esters, amides, proagents, active metabolites, isomers, fragments, analogs, and the like.

In some embodiments, the sigma-1 receptor agonist is PRE-084.

PRE-084

In some embodiments, sigma-1 receptor agonist is SA-4503.

SA-4503

In some embodiments the sigma-1 recentor agonist is ditolylguanidine ditolylguanidine In some embodiments, the sigma-1 receptor agonist is afobazole.

afobazole

In some aspects, disclosed herein are methods of modulating endothelial barrier function in a subject in need thereof, comprising: administering to the subject a therapeutically effective amount of a sigma-1 receptor agonist or a pharmaceutically acceptable salt thereof, wherein the subject is a human. In some embodiments, the human has an endothelial barrier disorder relating to dysregulated ATP metabolism. It should be understood that the balanced metabolism contributes to the maintenance of endothelial barrier integrity. Endothelial cells can rely more on glycolysis for energy production than mitochondrial oxidative phosphorylation as a measure to spare oxygen for delivery to the surrounding tissues. Therefore, "modulating endothelial barrier function" used herein refers to a treatment (for example, administering to a subject a therapeutically effective amount of a sigma-1 receptor agonist) aiming at maintaining or improving the endothelial barrier integrity by shifting metabolic production of ATP from oxidative mechanisms toward anaerobic glycolysis and maintaining or enhancing the endothelial barrier integrity by avoiding or limiting permeability of said barrier. The endothelial disorder described herein comprises ischemia, sepsis, edema, or inflammatory bowel disease. In some embodiments, the endothelial disorder is ischemia.

It is understood and herein contemplated that the endothelial barrier disorder relating to can arise from dysregulated ATP metabolism. Thus, disclosed herein are methods of modulating endothelial barrier function in a subject in need thereof, wherein the subject has an endothelial barrier disorder relating to dysregulated ATP metabolism, and wherein the endothelial barrier disorder is the result of dysregulated ATP metabolism. As the timing of the endothelial barrier disorder (e.g., ischemia) can often not be predicted, it should be understood the disclosed methods of treating, preventing, reducing, and/or inhibiting an endothelial barrier disorder relating to dysregulated ATP metabolism can be used following the dysregulation of ATP metabolism occurs, prior to or following the onset of the endothelial barrier disorder, to treat, prevent, inhibit, and/or reduce the endothelial barrier disorder. In some embodiments, the disclosed methods can be performed any time prior to the onset of the endothelial barrier disorder including prior to the dysregulation of ATP metabolism occurs. In one embodiments, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to the dysregulation of ATP metabolism occurs; concurrently with the dysregulation of ATP metabolism; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days after the dysregulation of ATP metabolism, but prior to onset of any symptoms of an endothelial barrier disorder (e.g., ischemia). In some embodiments, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days after onset of any symptoms of an endothelial barrier disorder (e.g. ischemia).

It should also be understood and is herein contemplated that the endothelial barrier disorder can occur concurrently with the dysregulation of ATP metabolism. In some embodiments, dysregulated ATP metabolism can be a symptom of the endothelial barrier disorder. Thus, disclosed herein are methods of modulating endothelial barrier in a subject in need thereof, wherein the subject has an endothelial barrier disorder relating to dysregulated ATP metabolism, wherein the endothelial barrier disorder occurs concurrently with the dysregulation of ATP metabolism. In one aspect, the disclosed methods can be employed 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to the dysregulation of ATP metabolism occurs; concurrently with the dysregulation of ATP metabolism ; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days after dysregulated ATP metabolism .

In some aspect, disclosed herein is a method of treating ischemia in a subject in need thereof, comprising: administering to the subject a therapeutically effective amount of a sigma-1 receptor agonist or a pharmaceutically acceptable salt thereof.

Dosing frequency for the therapeutic agent (e.g. PRE-084), or a pharmaceutically acceptable salt thereof, includes, but is not limited to, at least about once every three months, once every two months, once every month, once every three weeks, once every two weeks, or once a week. In some embodiments, the dosing frequency for the therapeutic agent, includes, but is not limited to, at last, about once every 14 days, once every 13 days, once every 12 days, once every 11 days, once every 10 days, once every 9 days, once every 8 days, once every 7 days, once every 6 days, once every 5 days, once every 4 days, once every 3 days, once every 2 days, or daily. In some embodiments, the interval between each administration is less than about a week, such as less than about any of 6, 5, 4, 3, 2, or 1 day. In some embodiments, the dosing frequency for the therapeutic agent includes, but is not limited to, at least once a day, twice a day, three times a day, or four times a day. In some embodiments, the interval between each administration is less than about 48 hours, 36 hours, 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is less than about 24 hours, 22 hours, 20 hours, 18 hours, 16 hours, 14 hours, 12 hours, 10 hours, 9 hours, 8 hours, 7 hours, 6 hours, or 5 hours. In some embodiments, the interval between each administration is constant. Administration can also be continuous and adjusted to maintaining a level of the compound within any desired and specified range.

The administration of the composition can be extended over an extended period of time, such as from about a month or shorter up to about three years or longer. For example, the dosing regimen can be extended over a period of any of about 2, 3, 4, 5, 6, 7, 8, 9, 10, 11, 12, 18, 24, 30, and 36 months. In some embodiments, there is no break in the dosing schedule. In some embodiments, the interval between a course of administration is no more than about a week.

EXAMPLES

Those skilled in the art will recognize or be able to ascertain using no more than routine experimentation, many equivalents to the specific embodiments of the invention described herein. While the invention has been described with reference to particular embodiments and implementations, it will be understood that various changes and additional variations may be made and equivalents may be substituted for elements thereof without departing from the scope of the invention or the inventive concept thereof. In addition, many modifications may be made to adapt a particular situation or device to the teachings of the invention without departing from the essential scope thereof. Such equivalents are intended to be encompassed by the following claims. It is intended that the invention not be limited to the particular implementations disclosed herein, but that the invention will include all implementations falling within the scope of the appended claims.

Example 1

PRE-084 increased human umbilical vein endothelial cell (HUVEC) barrier function in a concentration-dependent manner (FIG. 1A), showing its ability to protect the blood brain barrier (Liu D Y, et al. (2018) Sigma-1 receptor activation alleviates blood-brain barrier dysfunction in vascular dementia mice. *Exp Neurol* 308:90-99). The 100 μM concentration, which produced a maximal response (FIG. 1B), was chosen for subsequent experiments.

Figures 1A, 1B, 1C, 1D, 1E, 1F, 1G, 1H, 1I:
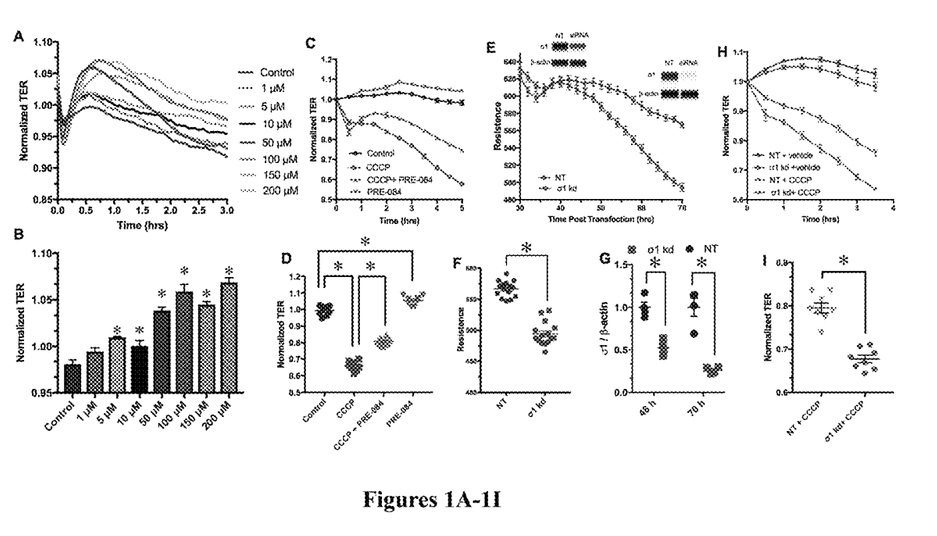

Because ATP depletion has been reported to disrupt the endothelial barrier (Unno N, et al. (1996) Hyperpermeability and ATP depletion induced by chronic hypoxia or glycolytic inhibition in Caco-2BBe monolayers. *Am J Physiol* 270(6 Pt 1):G1010-1021), assessment was performed to determine whether carbonyl cyanide m-chlorophenyl hydrazine (CCCP) induced mitochondrial insult causes barrier disruption and whether the barrier-enhancing properties of PRE-084 can counteract this effect. CCCP significantly lowered transendothelial electrical resistance (TER) (FIG. 1C) and pretreatment with PRE-084 significantly attenuated CCCP induced barrier disruption (FIG. 1D), indicating that sigma-1 receptor (σ1) activation can be beneficial in counteracting mitochondrial stress injuries. To further validate the contribution of σ1 to endothelial barrier function, siRNA was used to selectively reduce σ1 expression in HUVEC. At 48-h and 70-h post-transfection with σ1 siRNA, Western blots show 47% and 74% decreases in σ1 protein, respectively, compared to controls (FIG. 1E, insets). The degree of σ1 siRNA knockdown correlates to significant decreases in TER in σ1 siRNA-treated cells compared to control (FIG. 1E, FIG. 1F, and FIG. 1G). When CCCP is applied to HUVEC monolayers with diminished expression of σ1, the CCCP-induced barrier dysfunction is exacerbated compared to control HUVEC monolayers (FIG. 1H and FIG. 1I).

Figure 2A:
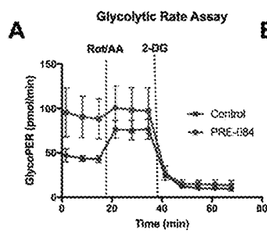
FIGS. 2A and 2B show glycolytic PER (glycoPER) and oxygen consumption rate (OCR) obtained from glycolytic rate assay of cells treated with 100 μM PRE-084 or vehicle for 3 hours.
Figure 2B:
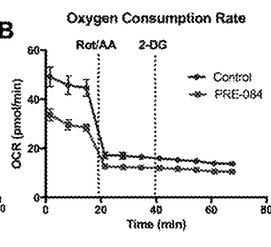
Figure 2C:
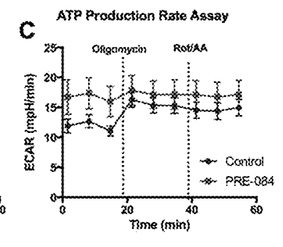
FIG. 2C shows extracellular acidification rate (ECAR) obtained from ATP rate assay.
Figure 2D:
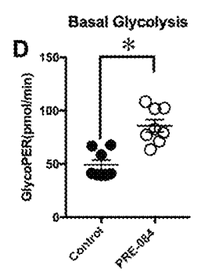
FIGS. 2D-2H show assay parameters obtained from the glycolytic rate assay.
Figure 2E:
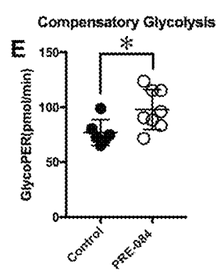
Figure 2F:
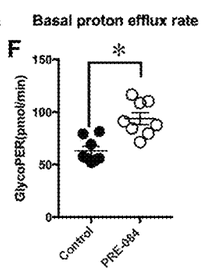
Figure 2G:
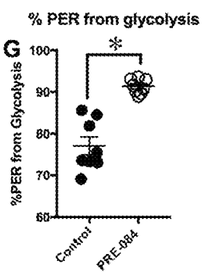
Figure 2H:
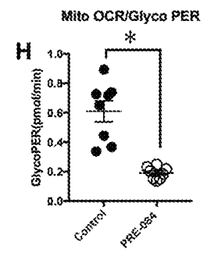
Figure 2I:
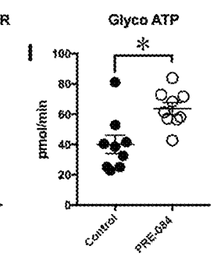
FIGS. 2I-2K show assay parameters from ATP rate assay. *P<0.05.
Figure 2J:
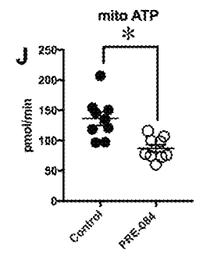
Figure 2K:
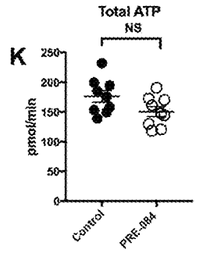
Figures 3A, 3B:
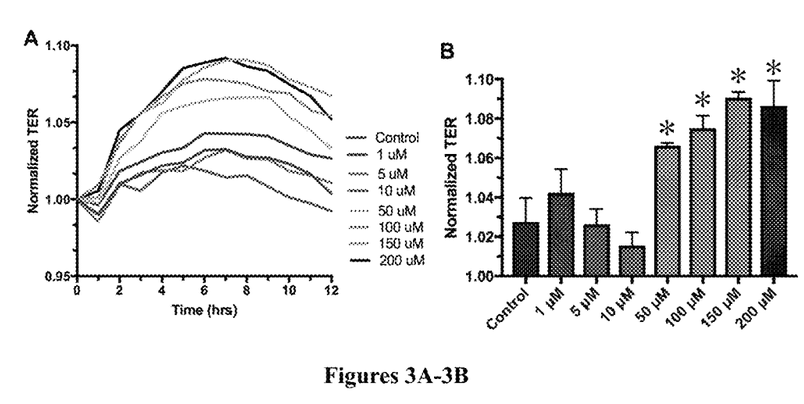
FIG. 3A shows traces showing the time course of changes in TER of HDMEC treated with the shown concentrations of PRE-084 treatments.
FIG. 3B shows the bar graph representing the differences in TER after 8 hours of PRE-084 treatment. *p<0.05. Analysis was done by One-Way ANOVA followed by Dunnett's multiple comparison test. N=4/group.
Figures 4A, 4B, 4C, 4D:
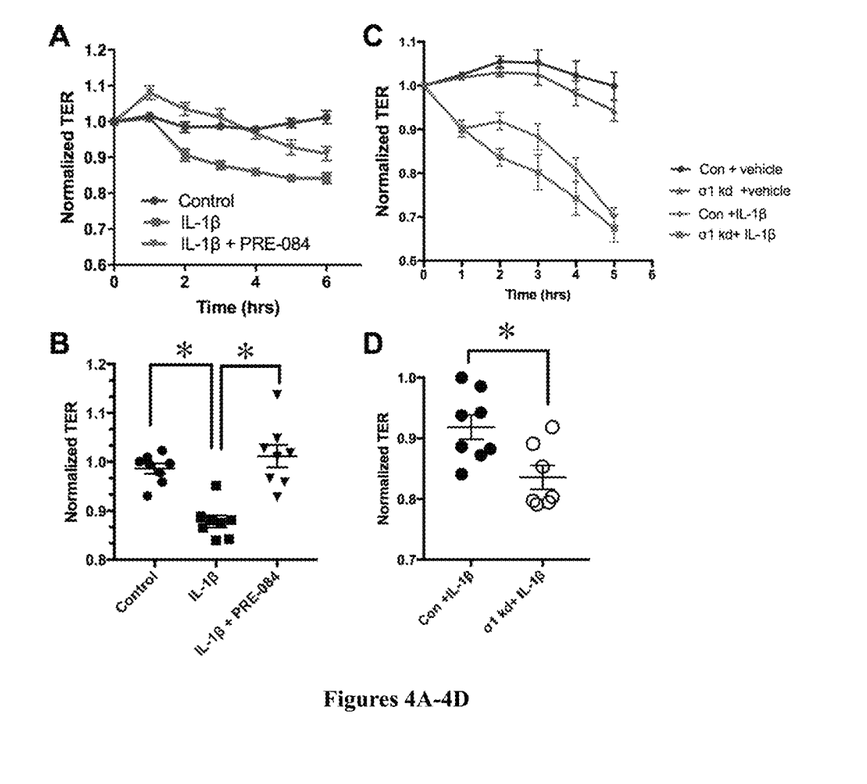
Figures 5A, 5B:
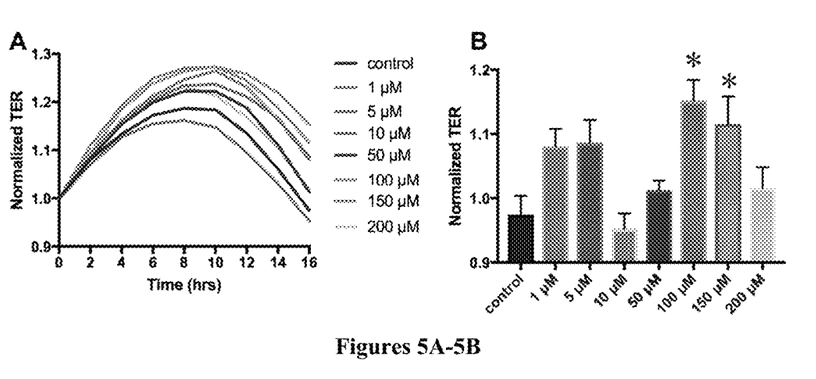
FIG. 5A shows traces showing the time course of changes in TER of HLMEC treated with the shown concentrations of PRE-084.
FIG. 5B shows the bar graph representing the differences in TER after 16 hours of PRE-084 treatment. *p<0.05. Analysis was done by One-Way ANOVA followed by Dunnett's multiple comparison test. N=3 or 4/group.
Figures 6A, 6B:
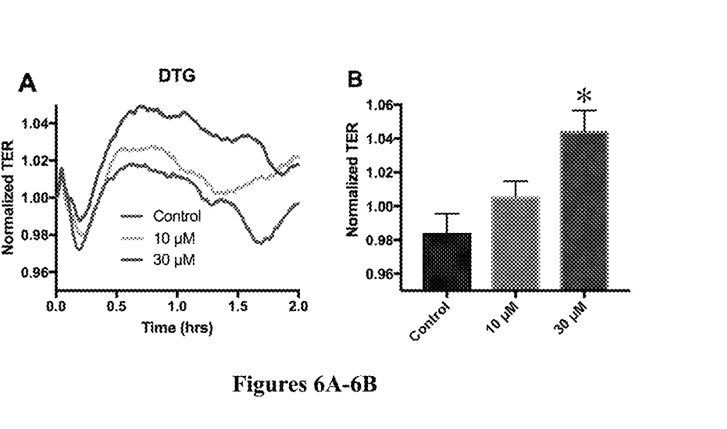
FIG. 6A shows trances showing the time course of changes in TER of HUVEC treated with the shown concentrations of DTG.
FIG. 6B shows the bar graph representing the differences in TER after 1.5 hour of DTG treatment. *p<0.05. Analysis was done by One-way ANOVA followed by Dunnett's comparison test. N=3/group.
Figure 7A:
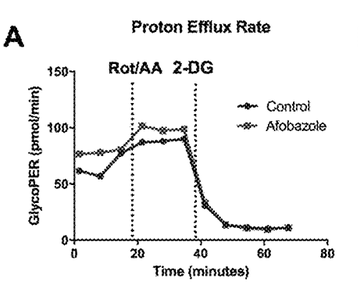
Figure 7B:
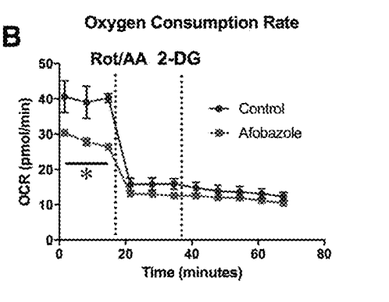
Figure 7C:
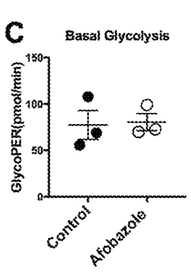
FIGS. 7C-7F show assay parameters obtained form glycolytic rate assay. Afobazole 300 µM or vehicle was used to treat cells 3 hours prior to the assay.
Figure 7D:
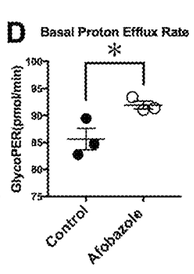
Figure 7E:
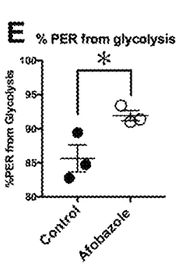
Figure 7F:
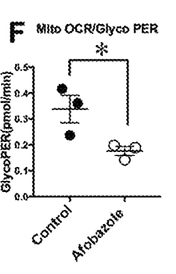

Given that activation of σ1 rescues the barrier disruption caused by CCCP, the contribution of σ1 to endothelial bioenergetics was assessed, focusing on glycolysis as it is generally thought to be the main energy production pathway in endothelial cells (Eelen G, et al. (2015) Endothelial cell metabolism in normal and diseased vasculature. *Circ Res* 116(7):1231-1244). The results show that HUVEC monolayers exposed to PRE-084 have a higher glycolytic proton efflux rate (GlycoPER) and higher extracellular acidification rate than controls (FIG. 2A and FIG. 2B). Furthermore, PRE-084 significantly elevates basal glycolysis, compensatory glycolysis, proton efflux rate (PER) from glycolysis, basal PER, and glycolytic ATP production (FIG. 2C-FIG. 2G). Notably, PRE-084 does not change the total amount of ATP (FIG. 2H). The results indicate that the barrier-enhancing properties caused by activation of σ1 are linked to a shift toward more glycolytic ATP production.

Example 2

The data show that σ1 activation elevates barrier function of endothelial cell monolayers and counteracts barrier dysfunction caused by disruption of mitochondrial ATP production. The data further indicate that σ1 activation enhances glycolysis and glycolytic ATP production. Taken together, these data show that σ1 activation preserves endothelial barrier function via a compensatory upregulation of glycolysis that maintains sufficient cellular levels of ATP to prevent barrier breakdown. This conclusion is consistent with a previous report that agents that enhance glycolysis, such as fructose, counteract CCCP-induced cell toxicity by promoting glycolytic ATP formation rather than by preserving mitochondrial membrane potential. This finding is also consistent with the notion that endothelial glycolytic ATP production is more favorable than mitochondrial ATP production because it spares oxygen for delivery to perivascular cells and minimizes endothelial reactive oxygen species (ROS) generation (Zecchin A, et al. (2017) How Endothelial Cells Adapt Their Metabolism to Form Vessels in Tumors. *Front Immunol* 8:1750). Also, glycolytic enzymes such as phospho-fructo-kinase are spatially associate with the peripheral endothelial actin cytoskeleton (De Bock K, et al. (2013) Role of PFKFB3-driven glycolysis in vessel sprouting. *Cell* 154(3):651-663), which has an active role promoting endothelial membrane protrusions that support junctional integrity (Breslin J W, et al. (2015) Involvement of local lamellipodia in endothelial barrier function. *PLoS One* 10(2):e0117970; Cao J, et al. (2017) Polarized actin and VE-cadherin dynamics regulate junctional remodeling and cell migration during sprouting angiogenesis. *Nat Commun* 8(1):2210). Computational models support the theory that localized ATP production at the endothelial cell periphery modulates such cellular rearrangements (Cruys B, et al. (2016) Glycolytic regulation of cell rearrangement in angiogenesis. *Nat Commun* 7:12240). Moreover, active spatiotemporal patterns of ATP-dependent signaling at the cell periphery is evident when endothelial cell monolayers are stimulated to enhance their barrier function (Zhang X E, et al. (2016) Activation of RhoA, but Not Rac1, Mediates Early Stages of S1P-Induced Endothelial Barrier Enhancement. *PLoS One* 11(5):e0155490).

Collectively, the data show a significant contribution of σ1 in endothelial barrier maintenance and protection in a chemically induced ischemia model. These data show for the first time that σ1 activation leads to enhanced glycolytic ATP production, which is tightly linked to endothelial barrier integrity. The work indicates that σ1 as a novel therapeutic target for ameliorating endothelial barrier dysfunction caused by ischemia, providing new mechanistic insight about the σ1 agonists as therapeutics for ischemia (Smith S B, et al. (2018) Sigma 1 receptor: A novel therapeutic target in retinal disease. *Prog Retin Eye Res* 67:130-149; Zamanillo D, et al. (2013) Sigma 1 receptor: a new therapeutic target for pain. *Eur J Pharmacol* 716(1-3):78-93; Mavlyutov T A, et al. (2017) The Sigma-1 Receptor-A Therapeutic Target for the Treatment of ALS? *Adv Exp Med Biol* 964:255-265).

Example 3

HUVEC and media were obtained from LifeLine cell technology, PRE-084 from Tocris Biotechne, and CCCP from Abcam. TER was determined with an Electrical Cell-Substrate Impedance Sensor (ECIS; Applied Biophysics). For transfection, 200 nM σ1 siRNA (SEQ ID NO: 2: GGCUUGAGCUCACCACCUA) or control non-targeting RNA (SEQ ID NO: 3: UGGUUUACAUGUUUUCCUA) purchased from Dharmacon was introduced with the Nucleofector II device (Lonza). Cell culture procedures, TER recordings, and protein isolation and transfection protocols have been previously described. Western blotting was done using WES (Protein Simple). Rabbit anti σ1 was purchased from Novus Biologicals NBP1-82479 and mouse anti (β-actin was from cell signaling #3700. Both primaries were used at 1:50 dilution. Seahorse xfp analyzer was used for glycolytic rate and ATP rate with assay kits (Agilent) according to manufacturer's instructions using 40.000 cells/well. Calculation of assay parameters was done using Wave software with its built-in report generators and statistical analysis was done using Prism 7.

SEQUENCES

```
Sigma-1 receptor gene sequence
                                                (SEQ ID NO: 1)
MQWAVGRRWAWAALLLAVAAVLTQVVWLWLGTQSFVFQREEIAQLARQY

AGLDHELAFSRLIVELRRLHPGHVLPDEELQWVFVNAGGWMGAMCLLHA

SLSEYVLLFGTALGSRGHSGRYWAEISDTIISGTFHQWREGTTKSEVFY

PGETVVHGPGEATAVEWGPNTWMVEYGRGVIPSTLAFALADTVFSTQDF

LTLFYTLRSYARGLRLELTTYLFGQDP

Sigma-1 receptor siRNA
                                                (SEQ ID NO: 2)
GGCUUGAGCUCACCACCUA Control siRNA
                                                (SEQ ID NO: 3)
UGGUUUACAUGUUUUCCUA
```

What is claimed is:

1. A method of treating a lymphatic endothelial barrier disorder in a subject in need thereof, comprising: administering to the subject a therapeutically effective amount of a sigma-1 receptor agonist or a pharmaceutically acceptable salt thereof, wherein the sigma-1 receptor agonist is PRE-084.

2. The method of claim 1, wherein the subject is a human.

3. The method of claim 1, wherein the lymphatic endothelial barrier disorder relates to dysregulated ATP metabolism.

* * * * *

SEQUENCE LISTING

```
<160> NUMBER OF SEQ ID NOS: 3

<210> SEQ ID NO 1
<211> LENGTH: 223
<212> TYPE: PRT
<213> ORGANISM: Homo sapiens

<400> SEQUENCE: 1

Met Gln Trp Ala Val Gly Arg Arg Trp Ala Trp Ala Ala Leu Leu Leu
1               5                   10                  15

Ala Val Ala Ala Val Leu Thr Gln Val Val Trp Leu Trp Leu Gly Thr
            20                  25                  30
```

```
Gln Ser Phe Val Phe Gln Arg Glu Glu Ile Ala Gln Leu Ala Arg Gln
        35                  40                  45
Tyr Ala Gly Leu Asp His Glu Leu Ala Phe Ser Arg Leu Ile Val Glu
    50                  55                  60
Leu Arg Arg Leu His Pro Gly His Val Leu Pro Asp Glu Glu Leu Gln
65                  70                  75                  80
Trp Val Phe Val Asn Ala Gly Gly Trp Met Gly Ala Met Cys Leu Leu
                85                  90                  95
His Ala Ser Leu Ser Glu Tyr Val Leu Leu Phe Gly Thr Ala Leu Gly
            100                 105                 110
Ser Arg Gly His Ser Gly Arg Tyr Trp Ala Glu Ile Ser Asp Thr Ile
            115                 120                 125
Ile Ser Gly Thr Phe His Gln Trp Arg Glu Gly Thr Thr Lys Ser Glu
    130                 135                 140
Val Phe Tyr Pro Gly Glu Thr Val Val His Gly Pro Gly Glu Ala Thr
145                 150                 155                 160
Ala Val Glu Trp Gly Pro Asn Thr Trp Met Val Glu Tyr Gly Arg Gly
                165                 170                 175
Val Ile Pro Ser Thr Leu Ala Phe Ala Leu Ala Asp Thr Val Phe Ser
            180                 185                 190
Thr Gln Asp Phe Leu Thr Leu Phe Tyr Thr Leu Arg Ser Tyr Ala Arg
            195                 200                 205
Gly Leu Arg Leu Glu Leu Thr Thr Tyr Leu Phe Gly Gln Asp Pro
            210                 215                 220

<210> SEQ ID NO 2
<211> LENGTH: 19
<212> TYPE: RNA
<213> ORGANISM: Artificial Sequence
<220> FEATURE:
<223> OTHER INFORMATION: Synthetic construct

<400> SEQUENCE: 2
ggcuugagcu caccaccua                                              19

<210> SEQ ID NO 3
<211> LENGTH: 19
<212> TYPE: RNA
<213> ORGANISM: Artificial Sequence
<220> FEATURE:
<223> OTHER INFORMATION: Synthetic construct

<400> SEQUENCE: 3
ugguuuacau guuuuccua                                              19
```